United States Patent
Kokones et al.

(10) Patent No.: US 9,002,472 B2
(45) Date of Patent: Apr. 7, 2015

(54) NEUROMODULATION HAVING NON-LINEAR DYNAMICS

(75) Inventors: Scott Kokones, Cleveland, OH (US); Bradford Curtis Fowler, McKenzie Bridge, OR (US); Donald Pfaff, New York, NY (US); Amy Wells Quinkert, New York, NY (US)

(73) Assignees: Intelect Medical, Inc., Cleveland, OH (US); The Rockefeller University, New York, NY (US)

( * ) Notice: Subject to any disclaimer, the term of this patent is extended or adjusted under 35 U.S.C. 154(b) by 1443 days.

(21) Appl. No.: 12/713,535

(22) Filed: Feb. 26, 2010

(65) Prior Publication Data

US 2011/0213439 A1 Sep. 1, 2011

(51) Int. Cl.
*A61N 1/36* (2006.01)
*A61N 1/05* (2006.01)

(52) U.S. Cl.
CPC ........ *A61N 1/36175* (2013.01); *A61N 1/36132* (2013.01); *A61N 1/36178* (2013.01); *A61N 1/3605* (2013.01); *A61N 1/3606* (2013.01); *A61N 1/0534* (2013.01); *A61N 1/36103* (2013.01)

(58) Field of Classification Search
CPC ............ A61N 1/3605; A61N 1/36057; A61N 1/36053; A61N 1/36128; A61N 1/36146; A61N 1/36175; A61N 1/36178; A61N 1/3606; A61N 1/36103; A61N 1/36132; A61N 1/36135
USPC .......................................... 607/45, 72, 73, 46
See application file for complete search history.

(56) References Cited

U.S. PATENT DOCUMENTS

| | | | |
|---|---|---|---|
| 7,231,254 B2 | 6/2007 | DiLorenzo | |
| 7,483,747 B2* | 1/2009 | Gliner et al. | 607/45 |
| 8,447,405 B2* | 5/2013 | Grill et al. | 607/45 |
| 2003/0212440 A1 | 11/2003 | Boveja | |
| 2005/0240242 A1* | 10/2005 | DiLorenzo | 607/45 |
| 2007/0167991 A1 | 7/2007 | DiLorenzo | |
| 2010/0121407 A1 | 5/2010 | Pfaff et al. | |

OTHER PUBLICATIONS

Arrieta-Cruz et al. "Mouse Model of Diffuse Brain Damage Following Anoxia, Evaluated by a New Assay of Generalized Arousal." Exp. Neurol. 205(2): 449-460, Jun. 2007.
Arrieta-Cruz et al. "Definition of Arousal and Mechanistic Studies in Intact and Brain-Damaged Mice." presentation at ARNMD (Association for Research in Nervous and Mental Disease), Dec. 2007.
Li et al. "Electrical Control of Epileptic Seizures." Journal of Clinical Neurophysiology 24(2): 197-204, Apr. 2007.

(Continued)

*Primary Examiner* — Tammie K Heller
(74) *Attorney, Agent, or Firm* — Lowe Graham Jones PLLC; Bruce E. Black (57) ABSTRACT

Methods, apparatuses, and software for operating such apparatuses, for neuromodulation in a live mammalian subject, such as a human patient, provide for applying electrical energy to a target site in the nervous system of the subject using a signal comprising a series of pulses, wherein the inter-pulse intervals are varied using the output of a deterministic, non-linear, dynamical system comprising one or more system control parameters. In certain embodiments, the target site may be a site in the brain involved in generalized CNS (central nervous system) arousal. The dynamical system may be capable of exhibiting chaotic behavior.

34 Claims, 10 Drawing Sheets

(56) References Cited

OTHER PUBLICATIONS

Pfaff et al. "A Theoretical Framework for CNS Arousal." BioEssays 29: 803-819, 2007.
Pfaff, "Brain Arousal and Information Theory: Neural and Genetic Mechanisms," pp. 51-53, Harvard University Press, 2005.
Pfaff et al. "Concepts and Mechanisms of Generalized Central Nervous System Arousal." Ann. N.Y. Acad. Sci. 1129: 1-7, May 2008.
Pfaff et al. "Mechanisms for the Regulation of State Changes in the Central Nervous System." Ann. N.Y. Acad. Sci. 1129: 1-7, May 2008.
Pfaff et al. "Generalized CNS Arousal in Animal and Human Brains." Jun. 2008.
Schiff, "Central Thalamic Contributions to Arousal Regulation and Neurological Disorders of Consciousness." Ann. N.Y. Acad. Sci. 1129: 105-118, May 2008.
Schiff et al. "Controlling Chaos in the Brain." Nature 370:615-620, Aug. 25, 1994.
Slutzky et al. "Manipulating Epileptiform Bursting in the Rat Hippocampus Using Chaos Control and Adaptive Techniques." IEEE Transactions on Biomedical Engineering 50(5): 559-570, May 2003.
Search Report dated Jan. 13, 2010, from corresponding International Patent Application No. PCT/US2009/063793.

* cited by examiner

NEUROMODULATION HAVING NON-LINEAR DYNAMICS

CROSS-REFERENCES TO RELATED APPLICATIONS

This application relates to U.S. Provisional Application No. 61/114,288 (filed on 13 Nov. 2008), which is incorporated by reference herein.

JOINT RESEARCH AGREEMENT

The claimed inventions were made by, on behalf of, and/or in connection with the following parties to a joint research agreement: The Rockefeller University and Intelect Medical, Inc. The agreement was in effect on or before the date the claimed inventions were made, and the claimed inventions were made as a result of activities undertaken within the scope of the agreement.

TECHNICAL FIELD

The present invention relates to the modulation of neural function and improving symptoms in patients suffering from certain medical conditions.

BACKGROUND

Electrical neuromodulation has been demonstrated to be useful for a variety of neurologic conditions. As such, attempts have been made to treat brain injury (e.g., due to trauma, hypoxia/anoxia, or stroke) by deep brain electrical stimulation. However, current approaches to neuromodulation for the treatment of brain injury and other conditions have had only limited efficacy. If electrical stimulation or other forms of neuromodulation are to have a greater impact on the treatment of brain injury (or other neurologic conditions), further improvements are needed.

SUMMARY

In one aspect, the present invention provides a method for neuromodulation in a live mammalian subject, comprising: applying electromagnetic energy to a site in the nervous system of the subject using a signal comprising a series of pulses, wherein the inter-pulse intervals are varied using the output of a deterministic, non-linear, dynamical system comprising one or more system control parameters. In certain embodiments, the electromagnetic energy is electrical. In certain embodiments, the dynamical system is a map ruled by a difference equation. In certain embodiments, the site in the nervous system is the brain.

In another aspect, the present invention provides a neuromodulation apparatus comprising: an electrode comprising an electrode contact; and a pulse generator coupled to the electrode; wherein the pulse generator is programmed to apply an electrical signal to the electrode contact, wherein the electrical signal comprises a series of pulses, wherein the inter-pulse intervals are varied using the output of a deterministic, non-linear, dynamical system having one or more system control parameters. In certain embodiments, the apparatus further comprises a physiologic sensor coupled to the pulse generator.

In another aspect, the present invention provides a computer-readable storage medium having executable instructions for performing the following: obtaining a set of solutions to one or more equations that rule a deterministic, non-linear, dynamical system having one or more system control parameters; and determining a set of inter-pulse intervals using the set of solutions, wherein the inter-pulse intervals define the time intervals between the pulses of a neuromodulation signal. In certain embodiments, the instructions further include controlling an apparatus to apply the neuromodulation signal to a site in the nervous system, such as the brain. In some embodiments, the coefficient of variation in the inter-pulse intervals is less than 1.0. In some embodiments, the executable instructions further perform the following: receiving a desired average frequency, desired level of variability, or both; wherein determining the inter-pulse intervals comprises setting the inter-pulse intervals such that the average frequency, level of variability, or both, of the neuromodulation signal substantially equals the desired value. In some embodiments, the executable instructions further perform the following: receiving a physiologic parameter; and modifying the set of inter-pulse intervals using an algorithm comprising the physiologic parameter. In some embodiments, the algorithm comprises changing a system control parameter. In some embodiments, the algorithm comprises obtaining a different set of solutions to the one or more equations.

The present invention also provides methods of improving the symptoms in a patient suffering from certain medical disorders by applying electromagnetic energy to a site in the nervous system of the patient using a signal comprising a series of pulses, wherein the inter-pulse intervals are varied using the output of a deterministic, non-linear, dynamical system comprising one or more system control parameters.

In another embodiment, the present invention provides a method of improving the symptoms in a patient suffering from stroke, comprising: applying electromagnetic energy to a site in the nervous system of the patient using a signal comprising a series of pulses, wherein the inter-pulse intervals are varied using the output of a deterministic, non-linear, dynamical system comprising one or more system control parameters; wherein the site in the nervous system is the cerebellum.

In another embodiment, the present invention provides a method of improving the symptoms in a patient suffering from depression, comprising: applying electromagnetic energy to a site in the nervous system of the patient using a signal comprising a series of pulses, wherein the inter-pulse intervals are varied using the output of a deterministic, non-linear, dynamical system comprising one or more system control parameters; wherein the site in the nervous system is cerebral cortex Area 25, cingulate cortex, or nucleus accumbens.

In another embodiment, the present invention provides a method of improving the symptoms in a patient suffering from a movement disorder, comprising: applying electromagnetic energy to a site in the nervous system of the patient using a signal comprising a series of pulses, wherein the inter-pulse intervals are varied using the output of a deterministic, non-linear, dynamical system comprising one or more system control parameters; wherein the site in the nervous system is the subthalamic nucleus or the globus pallidus interna.

BRIEF DESCRIPTION OF THE DRAWINGS

FIGS. 9A-9C show bar graphs representing locomotor activity data obtained from mice in the arousal assay experiments.

FIGS. 10A and 10B show bar graphs representing locomotor activity data obtained from mice in the telemetry-based experiments.

FIGS. 11A and 11B show the chaotic-interval signal patterns that were used in the experiments referred to in FIGS. 10A and 10B. FIG. 11A shows Chaotic Pattern 1 and FIG. 11B shows Chaotic Pattern 2.

DETAILED DESCRIPTION

The present invention relates to the modulation of neural function. In one aspect, the present invention provides a method for neuromodulation in a live mammalian subject, such as a human patient. The modulation of neural function can be useful in improving the symptoms of a patient suffering from a neurologic condition, such as, for example, traumatic brain injury, stroke, movement disorders and psychiatric disorders. The present invention relates to the modulation of neural function. In one aspect, the present invention provides a method for neuromodulation in a live mammalian subject, such as a human patient. The modulation of neural function can be useful in improving the symptoms of a patient suffering from a neurological deficit or disorder such as traumatic brain injury (TBI); stroke; movement disorders, such as, for example, Parkinson's Disease, spasticity, or essential tremor; and psychiatric disorders such as, for example, depression. For example, the methods of the present invention can be used to improve the symptoms of a TBI or stroke patient such as motor, language, and cognitive deficits. The method comprises applying electromagnetic energy to a target site in the nervous system, preferably the brain, of the subject using a signal comprising a series of pulses, wherein the inter-pulse intervals are varied using the output of a deterministic, non-linear, dynamical system comprising one or more system control parameters.

A dynamical system is a state space S (or phase space), a set of times T, and a rule R for evolution, that gives the consequent(s) to a state "s" (which is a member of S). The state space S has coordinates describing the state at any instant ("s") and the dynamical rule R specifies the immediate future of all state variables, given only the present values of those same state variables. Thus, a dynamical system can be considered a model describing the temporal evolution of a state space according to a rule for time evolution. Dynamical systems are deterministic if there is a unique consequent to every state (as opposed to stochastic or random if there is a probability distribution of possible consequents).

The neuromodulation may be targeted to any of various sites in the nervous system of the subject. In certain embodiments, the target site may be a site in the brain involved in generalized CNS (central nervous system) arousal. Generalized arousal is a global CNS state that is believed to be a primitive driving force behind motivated behavioral responses, cognitive functions, and emotional expressions. Earlier neuroscience work in this area has focused on understanding the arousal system by its individual circuit components, e.g., how individual stimuli evoke specific motor responses. However, more recent neuroscience work has addressed how large classes of salient stimuli from multiple sensory modalities cause changes in the entire state of the brain. New models have been proposed to explain how arousal responses encompassing all sensory modalities drive a wide range of motor and emotional responses with extreme sensitivity to the initial state of the system, and with very rapid and highly reliable responses. It is believed by the inventor(s) that non-linear dynamics theory (e.g., chaotic dynamics) best explains this robustly complex arousal system in the brain, which changes through with time and is subject to multiple feedback loops.

Figure 1:
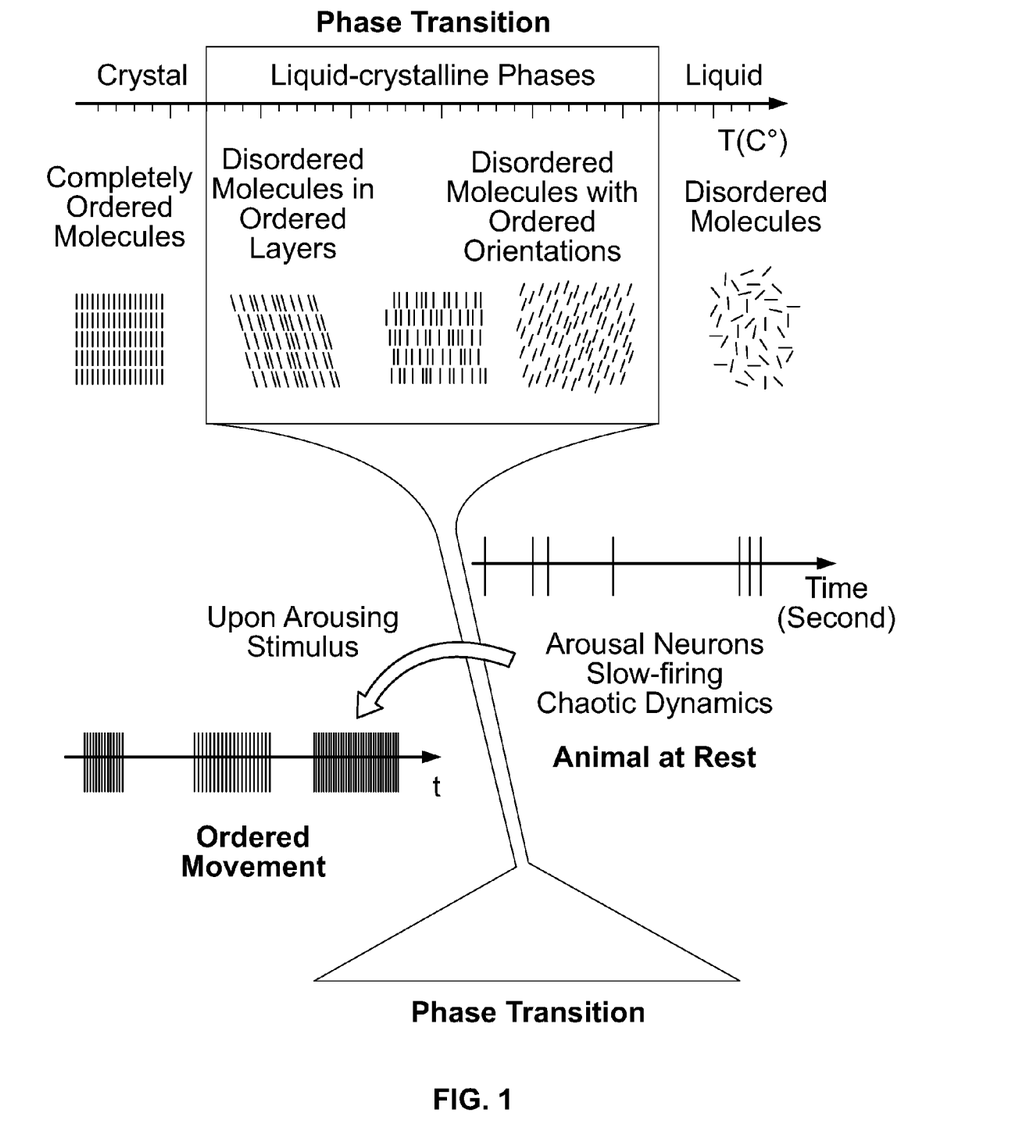
FIG. 1 shows a schematic illustration of a possible analogy comparing the brain's arousal function to different phases of matter.

Without intending to be bound by theory and for purposes of illustration only, FIG. 1 demonstrates a possible analogy that may be useful for understanding how a non-linear signal pattern may be effective in modulating brain or other neural function. This analogy compares the brain's arousal function to different phases of matter. The top portion of FIG. 1 shows a schematic illustration of the molecular ordering for liquid crystals ranging from liquid phase at higher temperatures (towards disordered molecules on the right side) to crystalline phase at lower temperatures (towards well-ordered molecules on the left side). T denotes the temperature. Between the liquid phase and the crystalline phase is the liquid crystalline phase, which is highly-sensitive because of its proximity to a phase transition to the liquid phase.

By analogy, in an animal at rest, large numbers of arousal-related neurons have their firing rates subject to chaotic dynamics so that the effects of small perturbations from the arousing stimulus can be amplified selectively and very rapidly. When a movement in response to that stimulus is initiated, cortical and subcortical controls take over, moving the system across the nearby phase transition into the domain of orderly, high rates of firing. Thus, analogous to phase transitions in a liquid crystal, CNS arousal systems, having "woken up" the brain to activate behavior, go through a phase transition and emerge under the control of orderly movement control systems. Based on the dynamics of brain arousal systems that are set forth here, it is believed that brain arousal systems are sensitive to neuromodulation with inter-pulse intervals that vary according to the output of a non-linear process, such as a chaotic process. During this phase transition of the arousal-related neurons into neural activity with orderly, high rates of firing, in certain embodiments of the present invention, the application of the electromagnetic energy may be temporarily stopped or reduced in intensity (e.g., reduced amplitude). This may be beneficial in facilitating the transition to orderly neural activity under the control of movement control systems. In some cases, this may be performed in a closed-loop system.

Figure 2A:
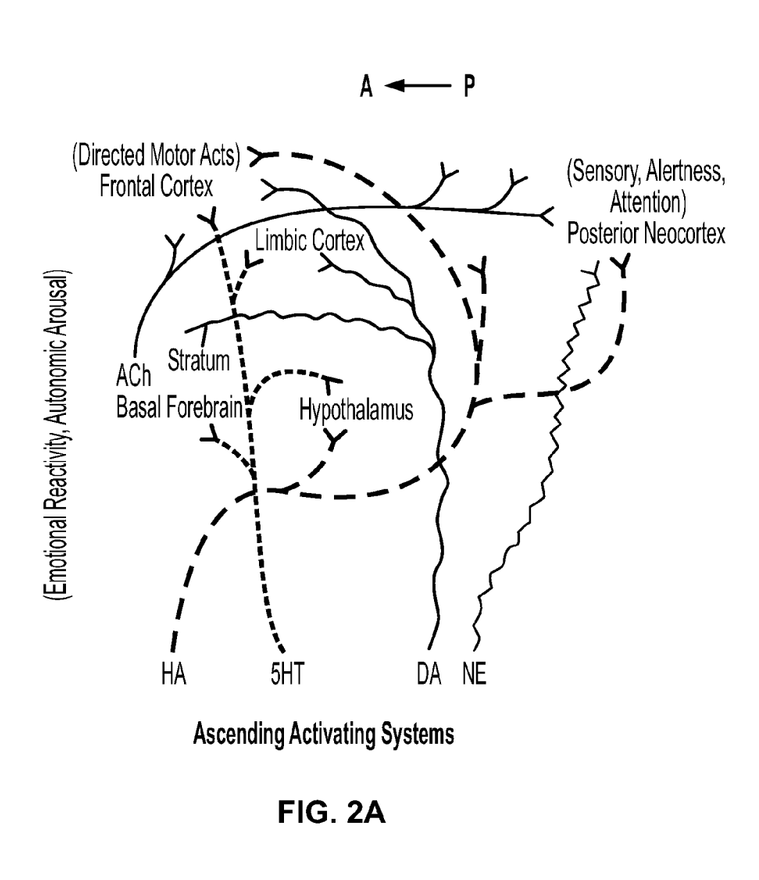
FIG. 2A shows a schematic illustration of ascending neuroanatomical pathways that may be involved in signaling arousal.

FIGS. 2A and 2B show the circuitry believed to be involved in CNS arousal mechanisms. As shown in FIG. 2A, the classical neuroanatomical pathways ascending from the lower brainstem toward the forebrain can signal arousal using norepinephrine, dopamine, serotonin, histamine, and acetylcholine as transmitters. Four sensory modalities feed these ascending pathways: touch (including pain), taste, vestibular, and auditory. These ascending pathways include norepinephrine-containing systems (NE) that tend to emphasize projections to the more posterior cerebral cortex (P, except for occipital cortex) and to support sensory alertness. Dopaminergic systems (DA) tend to project more strongly to the anterior frontal cortex (A) and to foster directed motor acts. Serotonergic (5HT) neurons project preferentially to a more ancient form of cortex ("limbic cortex") and hypothalamus, and to be involved in emotional behaviors and autonomic controls. Cholinergic neurons (ACh) in the basal forebrain support arousal by their widespread projections across the cerebral cortex. Histamine-producing neurons (HA) likewise have extremely widespread projections which actually originate in the hypothalamus and are strongly associated with increased CNS arousal.

Figure 2B:
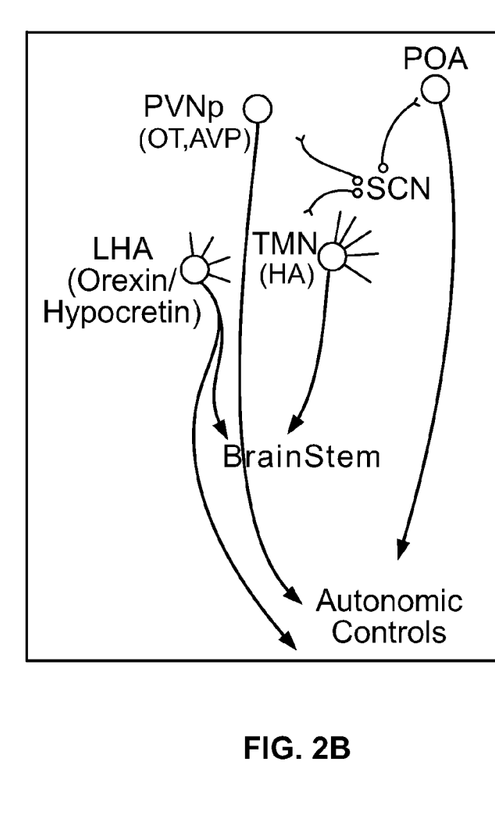
FIG. 2B shows a schematic illustration of descending neuroanatomical pathways that may be involved in CNS arousal.

Descending neuroanatomical pathways projecting from the forebrain toward the brainstem also play an important role in CNS arousal. As shown in FIG. 2B, lateral hypothalamic area (LHA) orexin neurons project down to monoamine-expressing cell groups in the lower brainstem and even to the spinal cord. Histamine (HA)-containing hypothalamic neurons in the tuberomammillary nucleus (TMN) have widespread projections, and receive inputs from a 'biological clock', the suprachiasmatic nucleus (SCN). Preoptic area (POA) neurons have descending axons which affect sleep and autonomic physiology. For example, nerve cells in the preoptic area connect to lower brain regions, which control the viscera. Likewise, the paraventricular nucleus of the hypothalamus has axonal projections which, in principle, could contribute to all aspects of arousal: cerebral cortical, autonomic, endocrine and behavioral. Oxytocin (OT) and arginine vasopressin (AVP)-expressing neurons in the parvocellular portion of the paraventricular hypothalamic nucleus (PVNp) control autonomic arousal through the lower brainstem and spinal cord, and affect EEG arousal through projections to locus coeruleus. In sum, while the ascending arousal systems have relatively few neurons, only sparse abilities to encode particular stimuli and are responsible for 'waking up' the cerebral cortex, descending arousal systems prepare the body for action by empowering reticulospinal neurons to activate our big posture-supporting trunk muscles and by activating autonomic systems.

Based on this understanding of CNS arousal circuitry, exemplary targets for neuromodulation according to the present invention include sites in the central nervous system, including the brain and spinal cord, and the peripheral nervous system, including spinal and autonomic nerves. Certain deep brain sites that could be targets include the thalamus (e.g., central, anterior, posterior, or intralaminar portions, such as the intralaminar nuclei of the thalamus), the subthalamic nucleus, the globus pallidus interna, basal forebrain (e.g., basal nucleus of Meynert), hypothalamus (e.g., anterior hypothalamic nucleus, tuberomammillary nucleus, suprachiasmatic nucleus, preoptic area, paraventricular nucleus, etc.), the brainstem (e.g., locus coeruleus, mesencephalic reticular formation, laterodorsal tegmentum (LDT) nuclei, pedunculopontine tegmentum (PPT) nuclei, etc.), the cerebellum, cerebral cortex Area 25, the nucleus accumbens, and cingulated cortex.

The inter-pulse intervals in the neuromodulation are varied using the output of a deterministic, non-linear, dynamical system comprising one or more system control parameters. Various types of deterministic, non-linear, dynamical systems are known in the art and are suitable for use in varying the inter-pulse intervals. For example, the dynamical system may be a discrete-time dynamical system that outputs a sequence $S_n$ at discrete times n=[1 . . . . N]. A deterministic evolution rule with discrete time and a continuous state space is called a "map" and its evolution is defined by the iteration:

$$s_{t+1} = f(s_t)$$

Figure 3A:
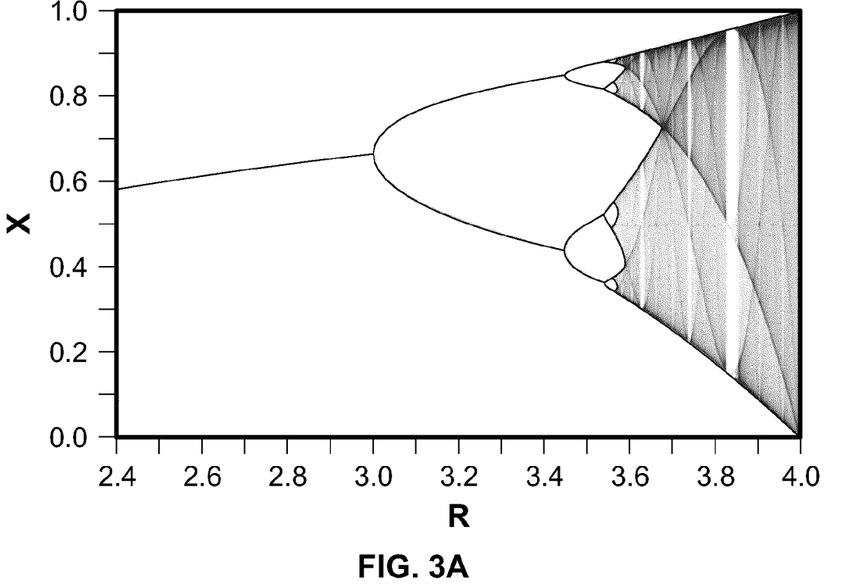
FIG. 3A shows the solutions to a logistic map with control parameter R in a range of 2.4 to 4.0.
Figure 3B:
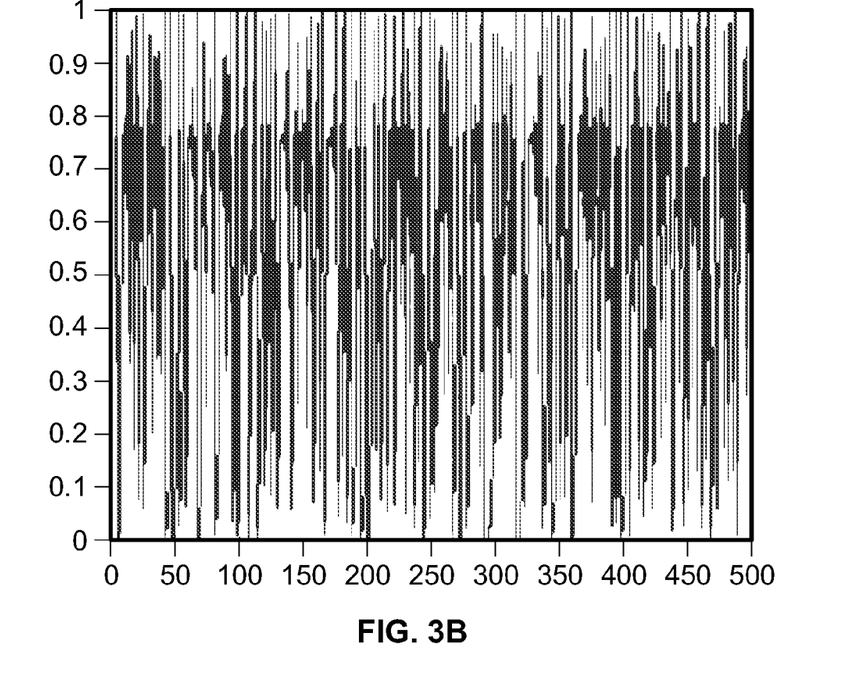
FIG. 3B shows a plot of the output values of the logistic map for R=4.0 through 500 iterations.

In some cases, the dynamical system may be capable of exhibiting chaotic behavior. One particular example of a time-discrete dynamical system capable of exhibiting chaotic behavior is the logistic map produced by the following difference equation:

$$X_{(n+1)} = R x_n (1 - x_n)$$

wherein the constant R is a system control parameter having a value between 0 and 4 (inclusive), and each $X_n$ is between 0 and 1, with an initial value being chosen to begin the iterative process. FIG. 3 shows the solutions to this logistic map and demonstrates that the logistic map exhibits either simple or complex behavior depending on the system control parameter R. The solutions become chaotic with R=3.5 and it is known that approximately 90% of R values between 3.57 and 4.0 results in chaotic behavior. FIG. 3B shows the output values $X_n$ of the logistic map for R=4.0 through 500 iterations.

Another example of a time-discrete dynamical system capable of exhibiting chaotic behavior example is a Hénon map produced by the following coupled difference equations:

$$x_{n+1} = 1 - \alpha x_n^2 + y_n$$

$$y_{n+1} = \beta x_n$$

Figure 4:
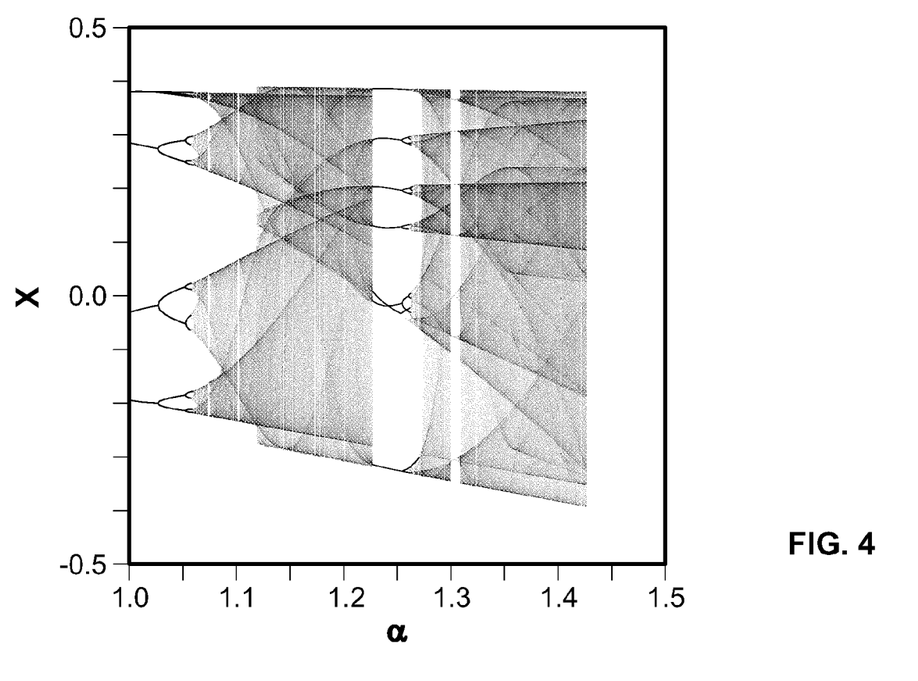
FIG. 4 shows the solutions to a Hénon map for values of control parameter a in a range of 1.0 to 1.5 and b=0.3.

This map depends on two system control parameters, $\alpha$ and $\beta$. FIG. 4 shows the solutions to the Hénon map for $\beta=0.3$, demonstrating that the map exhibits chaotic behavior for various values of $\alpha$. For example, the Hénon map is known to exhibit chaotic behavior at $\alpha=1.4$ and $\beta=0.3$.

Another example of a time-discrete dynamical system capable of exhibiting chaotic behavior is the Standard map defined by the difference equations:

$$p_{n+1} = p_n + K \sin(\theta_n)$$

$$\theta_{n+1} = \theta_n + p_{n+1}$$

where angular positions $p_n$ and $\theta_n$ are taken modulo $2\pi$ and the constant K is the system control parameter having a value >0.

Figure 5:
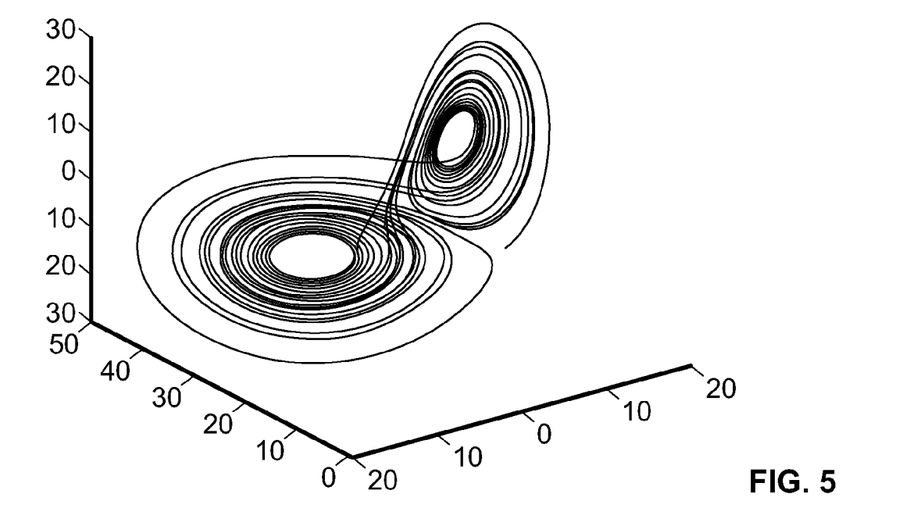
FIG. 5 shows a plot of the trajectory of the Lorenz system for σ=10, β=8/3, and ρ=28.

Other dynamical systems are on a manifold that is continuously differentiable with respect to time (such a dynamical system is called a "flow"). One such dynamical system is the Lorenz system governed by the following differential equations:

$$\frac{dx}{dt} = \sigma(y - x)$$

$$\frac{dy}{dt} = x(\rho - z) - y$$

$$\frac{dz}{dt} = xy - \beta z$$

where x, y, and z are the state variables; t is the independent variable; and the constants σ, ρ, and β are the system control parameters having a value >0. The Lorenz system is known to exhibit chaotic behavior for σ=10, β=8/3, and ρ=28 and the trajectory plot is shown in FIG. 5.

As demonstrated above, the system control parameter(s) of the dynamical system can be selected such that the dynamical system exhibits chaotic behavior. The term "chaotic behavior" means that the system exhibits long-term aperiodic behavior with a sensitivity to initial conditions, i.e., the fact that any two trajectories of the system, no matter how closely their initial starting positions are, will eventually diverge, and such divergence will be of exponential order. One measure of divergence of trajectories in a dynamical system is the Lyapunov exponent, which is a measure of the average rate of divergence/convergence of nearby trajectories. This can be used to determine whether the system is periodic, chaotic, or at equilibrium.

The Lyapunov exponent provides such a measure by comparing a reference orbit with a displaced orbit. Iterates of the initial condition $x_0$ are denoted the reference orbit and the displaced orbit is given by iterates of the initial condition $x_0$ where $d_0$ is a vector of infinitely small length denoting the displacement from the initial condition $x_0$. The initial orientation of the initial displacement is given by $u_0=d_0/|d_0|$. Using this notation, one way of calculating the Lyapunov exponent is as follows:

$$h(x_0, u_0) = \lim_{n \to \infty} \frac{1}{n} \ln(|d_n|/|d_0|)$$

where $d_n$ is the deviation of the displaced orbit from the reference orbit, given by the n'th iterate of $x_0$. A positive Lyapunov exponent indicates a chaotic state.

The neuromodulation may be implemented using any type of electromagnetic energy suitable for modulating neural tissue and in addition or alternatively, any form of energy suitable for modulating neural tissue. Such suitable types of electromagnetic energy include, for example, electrical, optical, magnetic, or radiofrequency (RF) energy. Alternatively, ultrasound energy could be used to implement the neuromodulation.

In certain embodiments, the present invention is implemented using electrical energy. The electrode may be any of those known in the art that are suitable for use in neuromodulation. The design characteristics of the electrode will vary depending upon the needs of the particular application, including such features as the number, direction, position, and/or arrangement of electrode contacts on the electrode; number of independent channels; and geometry and/or configuration of the electrode.

The electrical energy being applied may be characterized according to various parameters, including voltage, current amplitude, pulse width, average pulse frequency, train length, or waveform. Such signal parameters will vary depending upon the particular application. For example, the voltage may be selected from a range of ±0.1–10 V, pulse width may be selected from a range of 50-500 μs per phase, average pulse frequency may be selected from a range of 30-300 Hz, and current may be selected from a range of ±0.1 μA-5 mA. The electrical signal can have any suitable waveform, including square, sinusoidal, sawtooth, spiked, exponential rise/decay, or Gaussian, and where applicable, the signal may be monophasic, biphasic, multiphasic, or asymmetric. In some cases, the average pulse frequency is 200 Hz or greater.

Figure 6A:
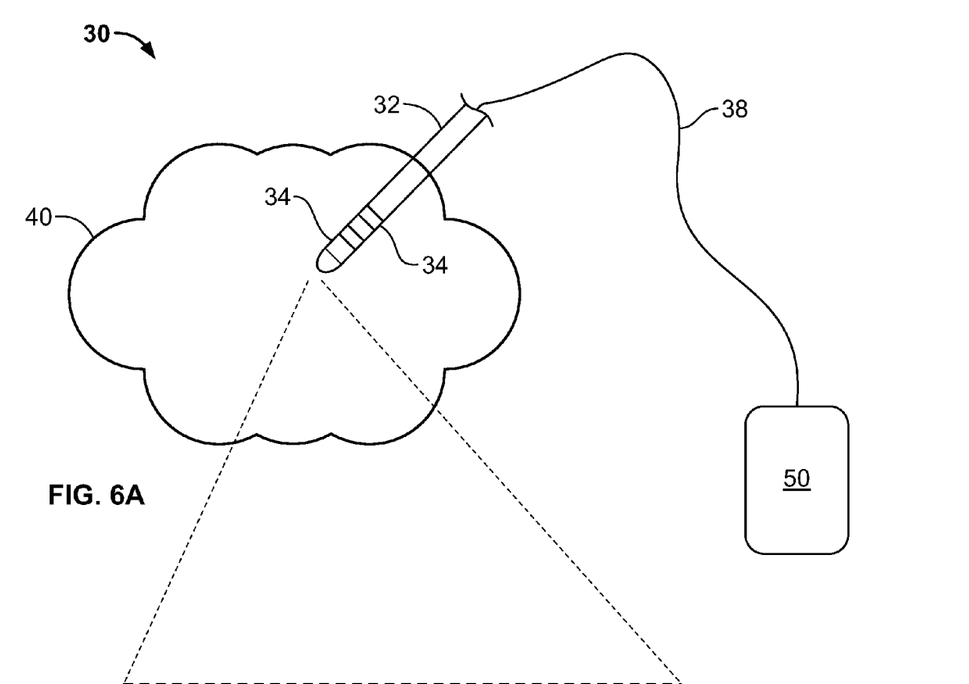
FIG. 6A shows a neuromodulation apparatus according to an embodiment of the present invention.
Figure 6B:
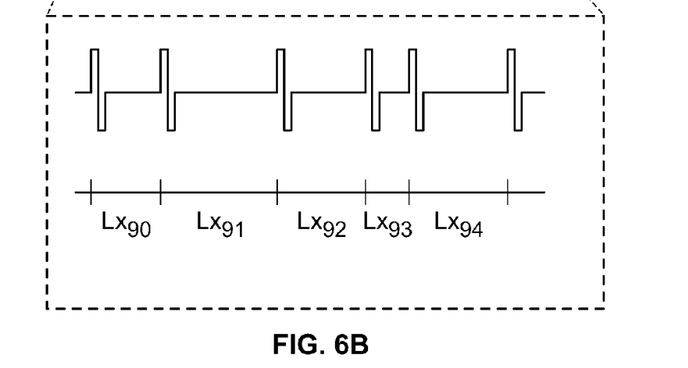
FIG. 6B shows a portion of the signal being applied by the neuromodulation apparatus.

Referring to the example embodiment shown in FIGS. 6A and 6B, a neuromodulation apparatus 30 includes an electrode 32 having electrode contacts 34, which is implanted in a brain site 40. A lead extension 38, which travels in a subcutaneous tunnel created by blunt dissection, connects electrode contacts 32 to a pulse generator 50 implanted in a subcutaneous pocket in the patient's chest area. As such, electrode contacts 34 are coupled to pulse generator 50. As used herein, the term "coupled" refers to a signaling relationship between the components in question, including direct connection or contact (e.g., via an electrically or optically conductive path), radio frequency (RF), infrared (IR), capacitive coupling, and inductive coupling to name a few.

Pulse generator 50 is programmed to generate an electrical signal based on outputted solutions $x_n$ to the logistic map above. The logistic map may be solved before or during the neuromodulation process. For example, solutions to the logistic map may be solved in advance and stored for later retrieval, or alternatively, the solutions may be calculated while the neuromodulation is in progress (e.g., in real-time). The output from the logistic map may be applied in any suitable manner to set the inter-pulse intervals. In some cases, the inter-pulse intervals may be some function of the output solutions ($x_n$). For example, output solutions may be scaled in an appropriate manner taking into consideration various factors such as the performance limitations of the neuromodulation equipment, the desired average pulse frequency and/or desired level of variability in the inter-pulse intervals (as according to any conventional statistical measure, such as coefficient of variance, variance, standard deviation, etc.), and the desired number of pulses in the train.

In operation, pulse generator 50 generates a signal and transmits the signal via lead extension 38 to electrode contacts 34 on electrode 32. FIG. 6B shows a schematic representation of the signal being applied at electrode contacts 34. The signal is a series of biphasic voltage pulses separated by time intervals $Lx_n$. Each $x_n$ is the n'th iterated output of the logistic equation with R set to a value between 3.57 and 4.0 such that the logistic equation generates a chaotic output. The output of the logistic equation for n=[90 ... 94] are arbitrarily selected for representation here. Each L is a constant used as a scalar multiplier to convert each $x_n$ to a time interval that is scaled to produce an electrical signal having a desired average pulse frequency (e.g., 50 Hz). Thus, the inter-pulse intervals in the signal shown in FIG. 6B are $Lx_{90}, Lx_{91}, Lx_{92}, Lx_{93}$, and so on.

Figure 7:
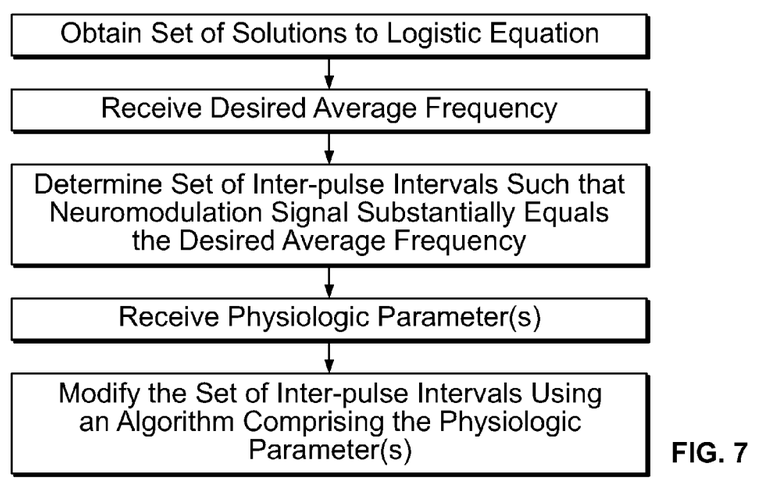
FIG. 7 shows a flowchart of the operation of a neuromodulation apparatus according to an embodiment.

The various functions and capabilities of neuromodulation apparatus 30 may be performed by electronic hardware, computer software (or firmware), or a combination of both. As such, neuromodulation apparatus 30 may include a computer-readable storage medium having executable instructions for performing the various processes as described and illustrated herein. The storage medium may be any type of computer-readable medium (i.e., one capable of being read by a computer), such as hard drive memory, flash memory, floppy disk memory, or optically-encoded memory (e.g., a compact disk, DVD-ROM, DVD±R, CD-ROM, CD±R). The systems disclosed herein may also include addressable memory (e.g., random access memory or cache memory) to store data and/or sets of instructions that may be included within, or be generated by, the executable instructions when they are executed by a processor on the respective platform. For example, pulse generator 50 may have executable instructions for performing the calculations needed to produce the desired neuromodulation signal. FIG. 7 shows a flowchart of how a neuromodulation apparatus may be operated according to an embodiment of the present invention.

In certain embodiments, the pulse generator is pre-programmed to deliver an electrical signal of a predetermined pattern to modulate neural function as described below or to treat neural conditions or disorders (i.e., to improve symptoms) as described below. In a preferred embodiment, the pulse generator is pre-programmed to deliver an electrical signal of a predetermined pattern to improve the function(s) (cognitive, motor, psychiatric, or other deficient functions) of a patient suffering from stroke or traumatic brain injury.

In certain embodiments, the present invention further comprises modifying the neuromodulation signal based on feedback data obtained from the subject. The feedback data may be any condition of the subject that is useful in measuring the effectiveness of the neuromodulation. For example, neuromodulation apparatus 60 above may have a sensor for detecting or measuring a physiologic parameter such as mechanical, motion, electrical, and/or chemical activity on or within the subject's body. Such physiologic parameters may be detected in various parts or functions of the body, including the nervous system, endocrine system, musculoskeletal system, respiratory system, circulatory system, urinary system, and/or digestive system. Examples of electrical activity that could be monitored include neuronal electrical activity, such as the electrophysiologic signals from the brain (e.g., EEG or electrode recordings), or muscular electrical activity (e.g., EMG). Examples of chemical activity that could be monitored include the detection or measurement of neurotransmitters, hormones, neuropeptides, or electrolytes in the subject's body (e.g., in the brain, blood, or cerebrospinal fluid). Other examples of physiologic parameters include heart rate, respiratory rate, blood pressure, blood oxygenation, etc. Sensors could also be used to detect motion or movement (e.g., for motor activity, tremors, gait, etc.).

In some cases, the feedback data may be indicative of the generalized arousal state of the subject. According to one proposed definition, generalized arousal has three components: (1) alertness to sensory stimuli in any one or more sensory modalities; (2) voluntary motor activity; and (3) emotional reactivity. All three components can be measured objectively by changes in physical activity. There are also various ways to quantify the arousal state. For example, according to one proposed mathematical model, arousal is a compound function of its principal components as follows:

$$A = F_g(A_g) \cdot [F_1(A_{C1}) + F_2(A_{C2}) \ldots + \ldots F_n(A_{Cn})]$$

where A is the state of global CNS arousal, $A_g$ is generalized arousal, each $A_{Cn}$ is a specific form of arousal (e.g., sexual, hunger, thirst, salt hunger, fear, and pain), and each $F_n$ is the relative force of that arousal component.

Feedback algorithms for modifying the neuromodulation signal according to the feedback data may increase or decrease the amount of arousal, depending upon the particular application. For example, the feedback algorithm may change the system control parameters of the dynamical system (e.g., "walking through" a series of R values for the logistic map), change the set of sequence terms used to vary the inter-pulse intervals, or change the number of sequence terms in a repeated-set used to vary the inter-pulse intervals.

The present invention can be used for neuromodulating a site in the nervous system of a live mammalian subject. Such neuromodulation includes activating or inhibiting neural tissue and includes modulating neural functions such as stimulating, depressing, or enhancing neural function (abnormal or normal) or treating neural conditions and disorders (i.e., to improve symptoms).

In preferred embodiments, the neurologic disorders are stroke or traumatic brain injury (for example, by neuromodulation of the thalamus, such as the intralaminar nuclei of the thalamus). In certain preferred embodiments, the methods of the present invention are used to improve cognitive, psychiatric, motor, and/or other functions in patients suffering from stroke and/or traumatic brain injury. In some embodiments, the neurologic disorders or conditions treated (i.e., to improve symptoms) by the present invention are characterized by arousal dysfunction. Such neurologic disorders or conditions that involve arousal dysfunction include, for example, coma, stupor, and sleep disorders. Non-limiting examples of sleep disorders include hypersomnia, insomnia, and narcolepsy. Other neurologic disorders include disorders of attention or mood such as, for example, depression, bipolar disorder, distractibility, inattention, locked-on vigilance, obsessiveness, and attention deficit hyperactivity disorder; disorders of affect or emotion such as, for example, anxiety or panic attacks, agitation, irritability, lack of restraint, logorrhea, aggression, apathy, akinesia, mutism, autism, dyslexia; disorders of psychic energy such as, for example, indifference, chronic fatigue syndrome, fibromyalgia, and chronic pain (including neuropathic pain); disorders of global cognitive function such as, for example, delirium, fugue states, dementia (e.g. age-related, Alzheimer's, multimodal, etc.), and vegetative state; impairments of focal conscious properties such as agnosia, apraxia, aphasia, loss of anticipation, and amnesia; and brain injury (e.g., due to trauma, stroke, infection, etc.).

In some cases, the present invention can be used for improving the symptoms of patients suffering from traumatic brain injury by neuromodulation of, for example, the thalamus (e.g., the intralaminar nuclei of the thalamus) or improving the symptoms of patients suffering from stroke by neuromodulation of, for example, the cerebellum and/or the thalamus (e.g., the intralaminar nuclei). Specific deficits that could be improved included motor, cognitive, and/or language function. Methods of the present invention can also be used for improving symptoms of patients suffering from movement disorders by neuromodulation of, for example, the globus pallidus, and/or subthalamic nuclei; or for improving symptoms of patients suffering from depression by neuromodulation of cerebral cortex area 25 (BA25), the cingulate cortex, and/or the nucleus accumbens

EXPERIMENTAL

Experimental trials were conducted in which mice were subjected to neuromodulation according to certain embodiments of the present invention. Electrodes were surgically implanted into the brains of the mice for deep brain stimulation. For the arousal assay experiments, the mice were individually housed inside an acrylic cage (i.e., arousal assay box) of a VersaMax animal monitoring system (AccuScan Instruments Inc., Columbus, Ohio). The cages were equipped with horizontal and vertical sensors containing a set of infrared photo beams distributed side-to-side and front-to-back. A VersaMax Analyzer (AccuScan Instruments Inc., Columbus, Ohio) was used to collect the beam status information from the arousal assay box. Each disruption of a beam was recorded as an activity count.

Locomotor activity was measured according to three main parameters: (a) horizontal activity (HACTV)=the total number of beam interruptions in the horizontal sensor within the observation time-frame; (b) total distance (TOTDIST)=the distance traveled around the entire cage in a continuous path, in cm, within the observation time-frame; and (c) vertical activity (VACTV)=the total number of beam interruptions of the vertical sensors within the observation time-frame.

To acclimate the mice, the mice were handled and plugged in without stimulation once a day for 3 or 4 days before stimulation began. On stimulation days, mice were handled using the same protocol and stimulated for 10 minutes before being returned to the arousal box. The mice were then subjected to at least one cycle of fixed-interval stimulation followed by chaotic-interval stimulation (e.g., fixed-interval on day 1, followed by chaotic-interval on day 2). The fixed-interval stimulations were provided at a frequency of 50 hz and the chaotic-interval stimulation was provided at an average frequency of 50 hz. The pulses were of 0.1 msec duration.

To generate the series of chaotic intervals, the output from the logistic equation was generated to a thousand or more terms. From this set of a thousand or more terms, a subset of contiguous terms were selected for use. For example, the set of terms may be the last 10, 15, or 50 output terms in the sequence generated by the logistic equation. Next, the maximum operable frequency f(based on instrument limitations) was determined and this was converted into the minimum operable inter-pulse intervals (IPI) using the relation 1/f=IPI. Next, a multiplier k was defined that sets the output terms to the minimum operable inter-pulse interval (IPI). Next, based on the number of pulses j desired in the train (e.g., j=10) and the multiplier k, a consecutive series of IPI's ($P_1$, $P_2$, $P_3$, ... $P_j$) that would produce a desired average frequency AF (e.g., 50 Hz) was calculated using the following formula:

$$AF = \frac{1}{k \cdot (P_1 + P_2 + P_3 + ... + P_j)}$$

Another set of experiments were performed on mice using a telemetry system (Data Sciences International, St. Paul, Minn.), which included signal receivers, signal transmitters, and data collection/analysis software. Electrodes were implanted in the brain of the mice and connected to the telemetry transmitter/receiver system. The system includes an activity sensor, as well as two channels for biopotentials, one for electroencephalogram (EEG) and one for electromyogram (EMG). As such, in addition to activity data, EEG (electroencephalography) and EMG (electromyogram) data were also collected and analyzed.

Before the start of each study, individually-housed implanted mice were placed on telemetry receivers within a grounded faraday cage. Transmitters were turned on right before recording started. The day after the start of recording, mice were stimulated 4 times a day. Recordings were stopped either 2 hours after the last stimulation or the next morning.

Figure 8A:
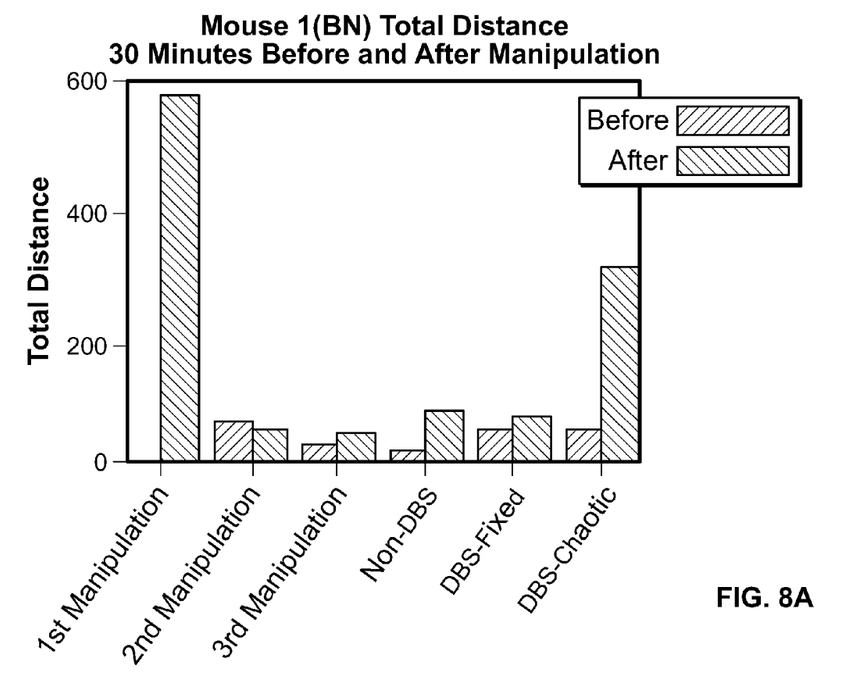
FIG. 8A shows bar graphs of the measured activity for a mouse that was subjected to neuromodulation according to an embodiment of the invention.
Figure 8B:
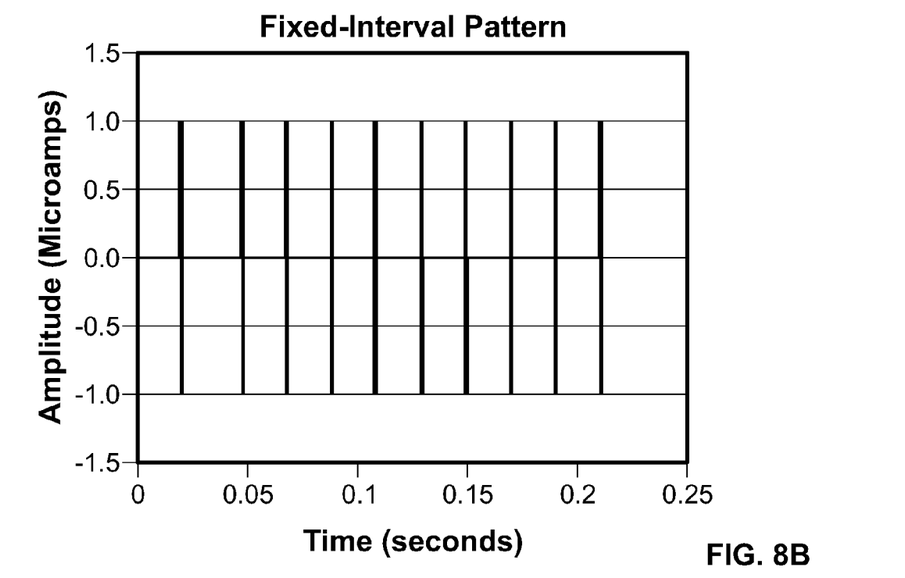
FIG. 8B shows the fixed-interval signal pattern used in the experiment.
Figure 8C:
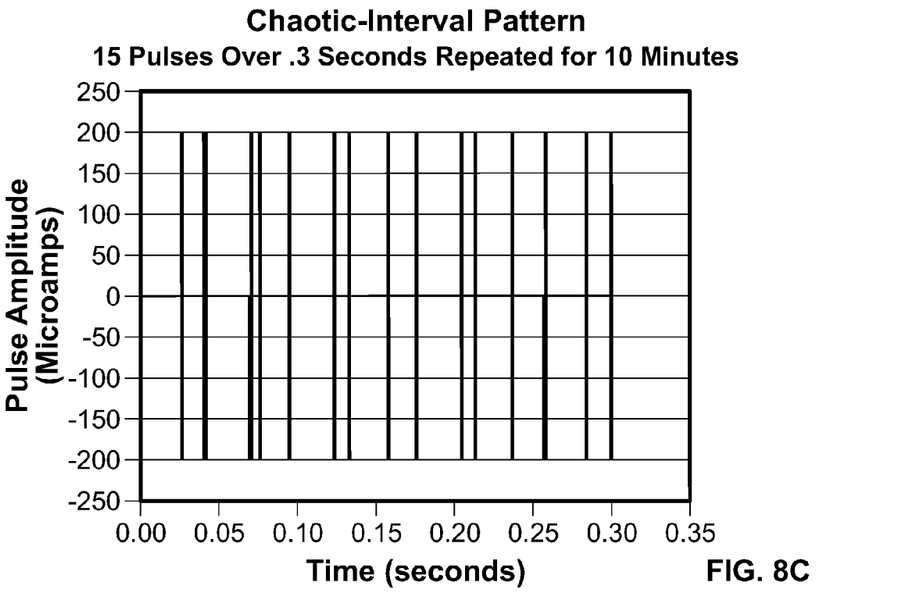
FIG. 8C shows the chaotic-interval signal pattern used in the experiment.

Within a few days after the last stimulation, the mice were perfused and the brains removed. After post-fixing and dehydration with 30% sucrose, the brains were sliced at 60 μm thickness, mounted on slides, and Nissl stained with cresyl violet dye to confirm placement of electrodes. FIGS. 8A-8C show the results of one of the mice in the arousal assay experiments in which the stimulation electrodes were implanted bilaterally in the basal (B) nucleus of Meynert. FIG. 8A show bar graphs of the activity data during the observation time-frame. After acclimation, the mouse was handled and activity recorded before and/or after manipulation. A sham stimulation (no stimulation) trial was performed with activity recorded 30 minutes before and/or after. Subsequently, the mouse was subjected to a fixed-frequency stimulation for 10 minutes at 130 Hz using biphasic square wave pulses, with activity recorded 30 minutes before and/or after. FIG. 8B depicts the pulse pattern used in the fixed-frequency stimulation. The mouse was then subjected to a chaotic pulse train stimulation for 10 minutes at an average frequency of 50 Hz using biphasic square wave pulses. FIG. 8C depicts the pulse pattern used in the chaotic stimulation, which was a series of 15 pulses spanning 0.3 seconds that were repeated for 10 minutes. As seen in FIG. 8A, the effectiveness of chaotic stimulation was dramatically better than fixed-frequency stimulation.

Figure 9A:
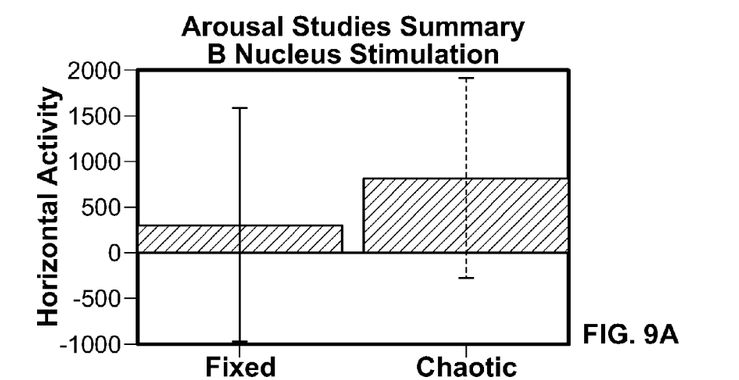
FIG. 9A shows the horizontal activity.
Figure 9B:
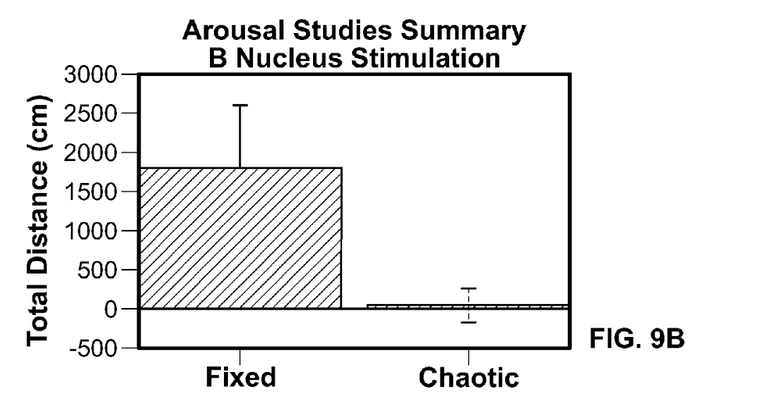
FIG. 9B shows the total distance.
Figure 9C:
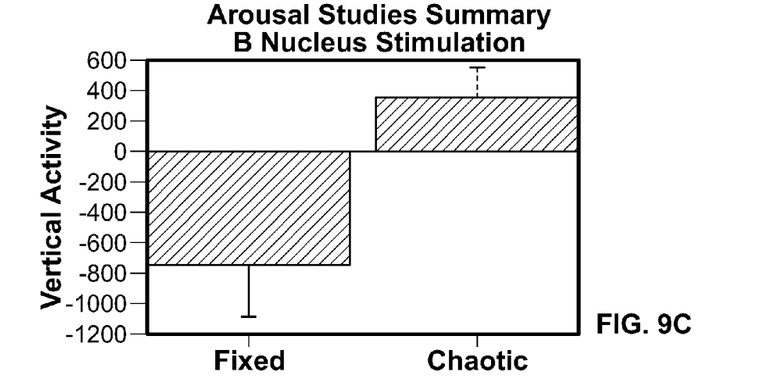
FIG. 9C shows the vertical activity.

FIGS. 9A-9C show bar graphs of data (obtained from at least 5 mice) from the arousal assay experiments. The bar graphs represent the difference in activity measured before and after stimulation. FIG. 9A shows the horizontal activity; FIG. 9B shows the total distance traveled; and FIG. 9C shows the vertical activity. In each case, the chaotic pulse train stimulation had a different effect on activity as compared to the fixed-frequency stimulation. For horizontal and vertical activity, the chaotic stimulation resulted in a greater increase in activity than fixed-frequency stimulation. For total distance, the chaotic stimulation resulted in a smaller increase in activity than the fixed-frequency stimulation.

Figure 10A:
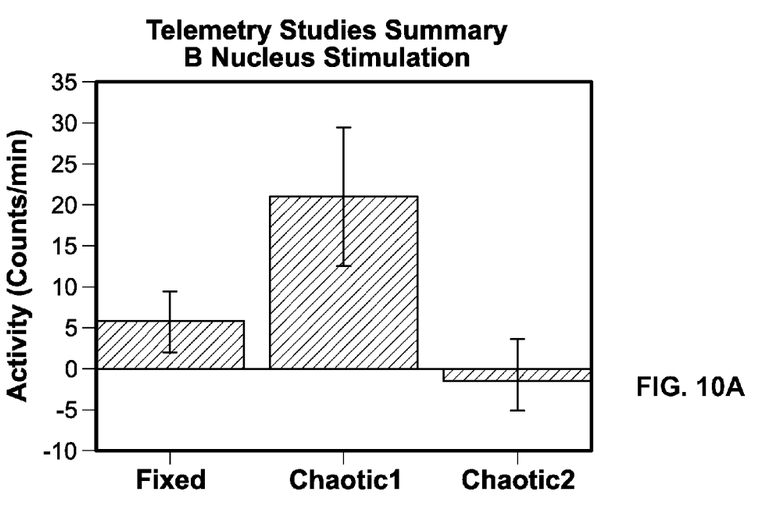
FIG. 10A shows the results for the mice stimulated in the basal nucleus of Meynert.
Figure 10B:
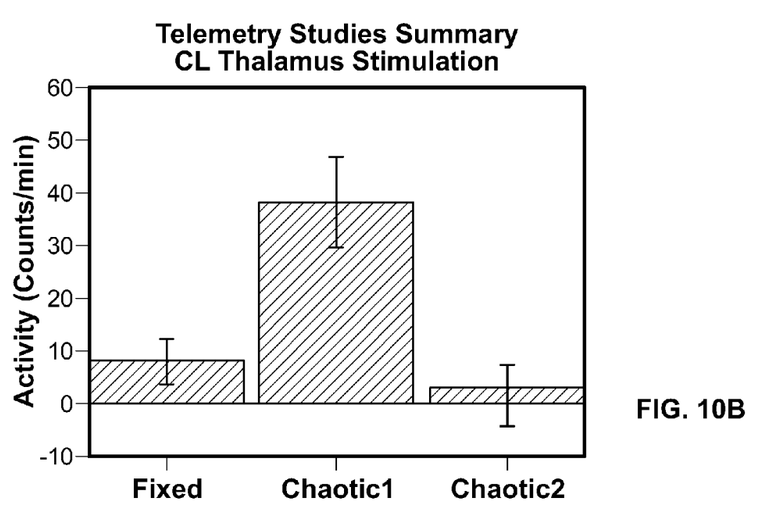
FIG. 10B shows the results for the mice stimulated in the central-lateral thalamus.
Figure 11A:
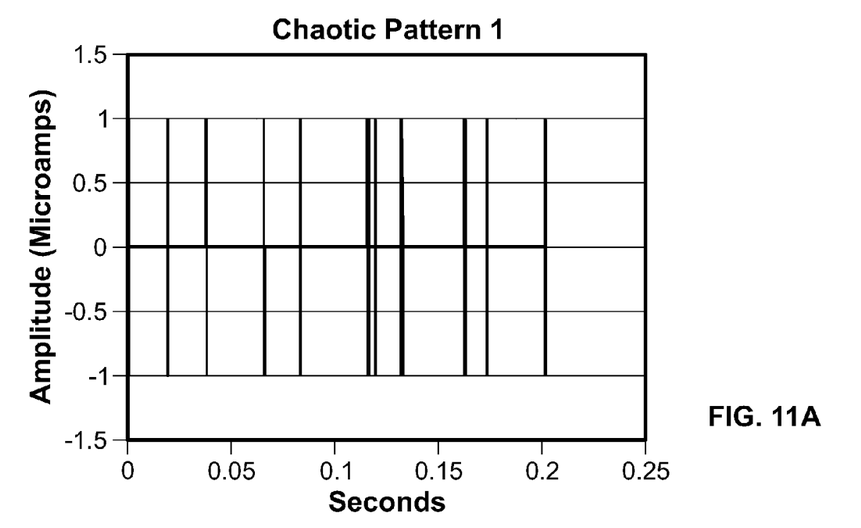
Figure 11B:
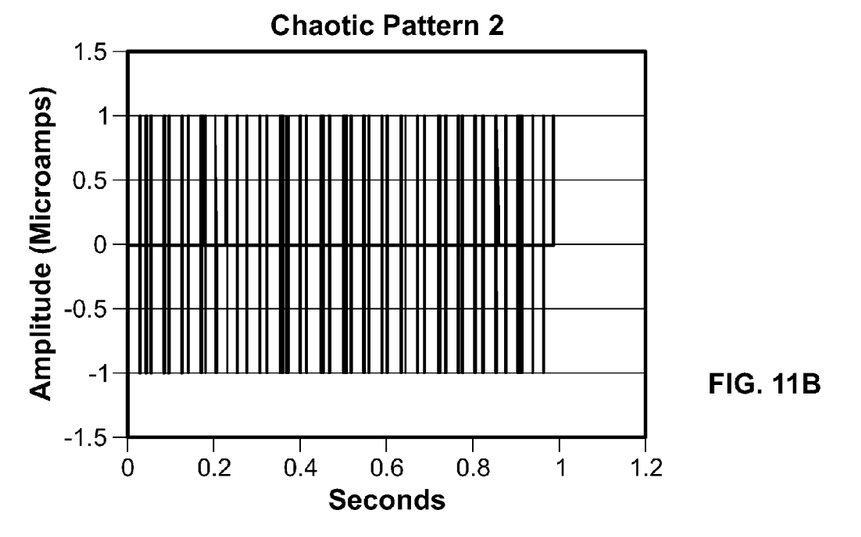

FIGS. 10A and 10B show bar graphs of data (obtained from at least 5 mice) from the telemetry-based experiments. The bar graphs represent the difference in activity measured before and after stimulation. FIG. 10A shows the activity results for fixed-frequency stimulation and two different chaotic train stimulations for mice with electrodes implanted in the basal (B) nucleus of Meynert. FIG. 10B shows the activity results for fixed-frequency stimulation and the two different chaotic train stimulations for mice with electrodes implanted in the central-lateral thalamus. As seen in FIGS. 10A and 10B, one of the chaotic pulse trains ("Chaotic 1") was substantially more effective than the fixed-frequency stimulation, while the other ("Chaotic 2") was not. FIG. 11A depicts the pulse pattern used in Chaotic 1 of FIGS. 10A and 10B, and FIG. 11B depicts the pulse pattern used in Chaotic 2. Chaotic Pattern 1 was a series of 10 pulses of 200 msec width each that was repeated for 10 minutes at 50 Hz average frequency. Chaotic Pattern 2 was a series of 50 pulses of 200 msec width each that was repeated for 10 minutes at 50 Hz average frequency.

Because the signal is based on the output of a dynamical system, some variance in the signal pattern is expected. But to enforce a pattern that is more orderly, in certain embodiments, the variability in the pulse width is such that the coefficient of variation (as an index of variability) is less than 1.0; and in some cases, less than 0.6. The coefficient of variation is the standard deviation (σ) of the inter-pulse intervals divided by the mean (μ) of the inter-pulse intervals (σ/μ). For example, since it is possible that different sets of contiguous terms (of the same set size) will have different levels of variability, the variability may be controlled by selecting a contiguous set of terms that will produce a signal pattern having the desired level of variability.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A computer-implemented method for neuromodulation in a live mammalian subject, comprising:
   triggering, by a processor, a leadwire to apply energy to a site in a nervous system of the subject in a series of pulses, wherein:
   inter-pulse intervals between the pulses vary;
   the triggering includes selecting, by the processor, the varying inter-pulse intervals according to output of an equation that defines a deterministic, non-linear, dynamical system of its output as varying over time by iterative execution of the equation using output of each iteration of its execution as input for its immediately succeeding iteration of its execution;
   a coefficient of variation in the inter-pulse intervals is less than 1.0; and
   the equation is one of:
      defined to produce output over time by its iterative execution such that the output over time exhibits chaotic behavior, the dynamical system having a positive Lyapunov exponent;

$$x_{(n+1)} = Rx_n(1-x_n);$$

a combination of $$x_{n+1} = 1 - \alpha x^2_n + y_n$$

and $$y_{n+1} = \beta x_n;$$

and a combination of $$P_{n+1} = P_n + K\sin(\theta_{n+1})$$

and $$\theta_{n+1} = \theta_n + P_{n+1}.$$

2. The method of claim 1, wherein the energy is electrical, and wherein the pulses are electrical pulses.

3. The method of claim 1, wherein the dynamical system is a map of inter-pulse interval values ruled by the equation, the equation being a difference equation.

4. The method of claim 3, wherein the difference equation is a logistic equation.

5. The method of claim 1, wherein the equation is defined to produce output over time by its iterative execution, such that the output over time exhibits the chaotic behavior.

6. The method of claim 5, wherein the dynamical system has the positive Lyapunov exponent.

7. The method of claim 1, wherein the site in the nervous system is involved in central nervous system arousal.

8. The method of claim 7, wherein the nervous system site is a site in the brain.

9. The method of claim 8, wherein the brain site is selected from the group consisting of:
   thalamus, basal forebrain, hypothalamus, and brainstem.

10. The method of claim 1, further comprising obtaining feedback data from the subject and modifying the neuromodulation according to the feedback data.

11. The method of claim 10, wherein the feedback data comprises a physiological parameter.

12. The method of claim 11, wherein the physiological parameter is electrophysiological activity in the subject's brain.

13. The method of claim 10, wherein modifying the neuromodulation comprises adjusting a system control parameter.

14. The method of claim 1, wherein the inter-pulse intervals are varied using a finite set of contiguous terms outputted by the dynamical system, and the finite set of contiguous terms are used in a repeating pattern for the triggering of the leadwire.

15. The method of claim 1, wherein the coefficient of variation in the inter-pulse intervals is less than 0.6.

16. The method of claim 1, wherein the site in the nervous system is the thalamus.

17. The method of claim 1, wherein the site in the nervous system is the intralaminar nuclei of the thalamus.

18. The method of claim 1, wherein the site in the nervous system is the cerebellum.

19. The method of claim 1, wherein the site in the nervous system is the cerebral cortex Area 25, cingulate cortex, or nucleus accumbens.

20. The method of claim 1, wherein the site in the nervous system is the subthalamic nucleus or the globus pallidus interna.

21. The method of claim 1, further comprising:
   obtaining from a physiologic sensor a physiologic parameter, and
   modifying the pulses according to the physiologic parameter.

22. The method of claim 1, wherein the output of the equation is non-cyclic.

23. The method of claim 22, wherein the processor selects a finite set of contiguous output of the equation and cycles the selected finite set of contiguous output as a repeating pattern of inter-pulse intervals for the triggering.

24. The method of claim 1, wherein the equation is $X_{(n+1)} = Rx_n(1-x_n)$.

25. The method of claim 1, wherein the equation is the combination of $$x_{n+1} = 1 - \alpha x^2_n + y_n$$

and $$y_{n+1} = \beta x_n.$$

26. The method of claim 1, wherein the equation is the combination of $$P_{n+1} = P_n + K\sin(\theta_{n+1})$$

and $$\theta_{n+1} = \theta_n + P_{n+1}.$$

27. A computer-implemented method for neuromodulation in a live mammalian subject, comprising:
   triggering, by a processor, a leadwire to apply energy to a site in a nervous system of the subject in a series of pulses;
   obtaining feedback data from the subject; and
   modifying the neuromodulation according to the feedback data;
   wherein:
      inter-pulse intervals between the pulses vary;
      the triggering includes selecting, by the processor, the varying inter-pulse intervals according to output of an equation that defines a deterministic, non-linear, dynamical system of its output as varying over time by iterative execution of the equation using output of each iteration of its execution as input for its immediately succeeding iteration of its execution;
a coefficient of variation in the inter-pulse intervals is less than 1.0; and
modifying the neuromodulation comprises using a different set of output from the dynamical system to vary the inter-pulse intervals.

28. A computer-implemented method for neuromodulation in a live mammalian subject, comprising:
triggering, by a processor, a leadwire to apply energy to a site in a nervous system of the subject in a series of pulses;
obtaining feedback data from the subject; and
modifying the neuromodulation according to the feedback data;
wherein:
inter-pulse intervals between the pulses vary;
the triggering includes selecting, by the processor, the varying inter-pulse intervals according to output of an equation that defines a deterministic, non-linear, dynamical system of its output as varying over time by iterative execution of the equation using output of each iteration of its execution as input for its immediately succeeding iteration of its execution;
a coefficient of variation in the inter-pulse intervals is less than 1.0;
obtaining the feedback data comprises detecting neural activity in arousal-related neurons in the subject's brain; and
modifying the neuromodulation comprises stopping or reducing the intensity of the applied energy upon the detection of orderly neural activity in the arousal-related neurons.

29. A neuromodulation apparatus comprising:
an electrode comprising an electrode contact; and
a pulse generator coupled to the electrode;
wherein:
the pulse generator is programmed to apply an electrical signal to the electrode contact for applying energy to a site in a nervous system of a subject;
the electrical signal comprises a series of pulses with inter-pulse intervals that are varied;
the pulse generator is configured to select the varying inter-pulse intervals according to output of an equation that defines a deterministic, non-linear, dynamical system of its output as varying over time by iterative execution of the equation using output of each iteration of its execution as input for its immediately succeeding iteration of its execution;
the coefficient of variation in the inter-pulse intervals is less than 1.0; and
the equation is one of:
defined to produce output over time by its iterative execution such that the output over time exhibits chaotic behavior, the dynamical system having a positive Lyapunov exponent;

$$x_{(n+1)} = Rx_n(1-x_n);$$

a combination of $$x_{n+1} = 1 - \alpha x^2_n + y_n \text{ and } y_{n+1} = \beta x_n;$$

and a combination of $$P_{n+1} = P_n + K \sin(\theta_{n+1})$$

and $$\theta_{n+1} = \theta_n + P_{n+1}.$$

30. The apparatus of claim 29, wherein the dynamical system is a map ruled by a difference equation.

31. The apparatus of claim 29, wherein the one or more system control parameters for the dynamical system are selected such that the dynamical system exhibits chaotic behavior.

32. A computer-implemented method for neuromodulation in a live mammalian subject, comprising:
iteratively executing, by a computer processor, a difference equation whose output, after output of a first of the iterations, is calculated using a value of a prior output of the difference equation as an input of the difference equation; and
triggering, by the processor, a leadwire to apply electrical energy to a site in a nervous system of the subject in a series of pulses whose inter-pulse intervals vary, wherein the triggering is performed based on the iterative execution such that each of the inter-pulse intervals is a respective value output by a respective executed iteration of the equation;
wherein:
a coefficient of variation in the inter-pulse intervals is less than 1.0; and
the equation is one of:
defined to produce output over time by its iterative execution such that the output over time exhibits chaotic behavior, the dynamical system having a positive Lyapunov exponent;

$$X_{(n+1)} = Rx_n(1-x_n);$$

a combination of $$x_{n+1} = 1 - \alpha x^2_n + y_n$$

and $$y_{n+1} = \beta x_n;$$

and a combination of $$P_{n+1} = P_n + K \sin(\theta_{n+1})$$

and $$\theta_{n+1} = \theta_n + P_{n+1}.$$

33. The method of claim 32, wherein the difference equation defines a deterministic, non-linear, dynamical system.

34. The method of claim 32, wherein the equation is defined to produce varying output by iterative execution thereof over time.

* * * * *